United States Patent [19]

Horrobin

[11] Patent Number: 5,580,556
[45] Date of Patent: Dec. 3, 1996

[54] PHARMACEUTICAL COMPOSITIONS CONTAINING INTERFERONS AND FATTY ACIDS

[75] Inventor: David F. Horrobin, Guildford, England

[73] Assignee: Efamol Holdings PLC, England

[21] Appl. No.: 367,819

[22] Filed: Jan. 3, 1995

Related U.S. Application Data

[63] Continuation of Ser. No. 15,035, Feb. 8, 1993, abandoned, which is a continuation of Ser. No. 561,992, Aug. 2, 1990, abandoned.

[30] Foreign Application Priority Data

Aug. 10, 1989 [GB] United Kingdom ............... 8918294

[51] Int. Cl.$^6$ ................................................. A61K 38/21
[52] U.S. Cl. ................ 424/85.4; 424/85.5; 424/85.6; 424/85.7
[58] Field of Search ..................... 424/85.4, 85.5, 424/85.6, 85.7

[56] References Cited

U.S. PATENT DOCUMENTS

| | | | |
|---|---|---|---|
| 4,309,415 | 1/1992 | Horrobin | 424/85 |
| 4,513,008 | 4/1985 | Revici et al. | 514/560 |
| 4,931,468 | 6/1990 | Horrobin | 514/560 |

FOREIGN PATENT DOCUMENTS

| | | |
|---|---|---|
| 0004770 | 10/1979 | European Pat. Off. . |
| 0295954 | 12/1988 | European Pat. Off. . |
| 0364094 | 4/1990 | European Pat. Off. . |
| 2134782 | 8/1984 | United Kingdom . |

OTHER PUBLICATIONS

Mauku et al Brit. J. of Dermatol. (1984) vol. 110, pp. 643–648.
Chandrabose et al Sci, vol. 212 (Apr. 1981) pp. 329–331.
Pottathil et al PNAS, USA vol. 77, No. 9 pp. 5437–5440, Sep. 1980.
Anals New York Academy of Sciences Johnson et al "Structural Basis for Arachidonic Acid Second Messenger Signal in Gamma–Interferon Induction" pp. 208–217.
Chemical Abstracts, 110(1), 1989, 578 g and Ann. NY. Acad. Sci 1988, 524.
Harper's Biochemistry, 23rd Edn, Eds. Murray et al., Appleton & Lange, pp. 232–240, 1993.
Chandrabose et al., Prostaglandins Relat. Lipids, vol. 2, pp. 345–364, 1982.
Brideau et al., J. Int. Res., vol. 3(4) pp. 409–415, 1983.
Forti et al., Prostaglandins, vol. 26(3), pp. 409–420, 1983.
"Immunology", Roitt et al., Publishers Mosby, Baltimore, Third Edn., pp. 8.12–8.15, 1993.

*Primary Examiner*—Chhaya D. Sayala
*Attorney, Agent, or Firm*—Nixon & Vanderhye

[57] ABSTRACT

The use of one or more of gamma-linolenic acid, dihomo-gamma-linolenic acid and arachidonic acid for the manufacture of a medicament for use in enhancement of the anti-viral, anti-cancer or anti-inflammatory effects of interferons; the medicament containing or being for use with a medicament containing one or more interferons when not solely for enhancement of the effect of endogenous interferons.

11 Claims, No Drawings

PHARMACEUTICAL COMPOSITIONS CONTAINING INTERFERONS AND FATTY ACIDS

This is a continuation of application Ser. No. 08/015,035, filed Feb. 8, 1993 which is a continuation of 07/561,992 filed Aug. 2, 1990, both now abandoned.

FIELD OF THE INVENTION

The invention relates to the enhancement of the bodily action of interferons.

GENERAL BACKGROUND

The outline of production of 1-series and 2-series PGs in the body is believed to be as shown in the following diagram:

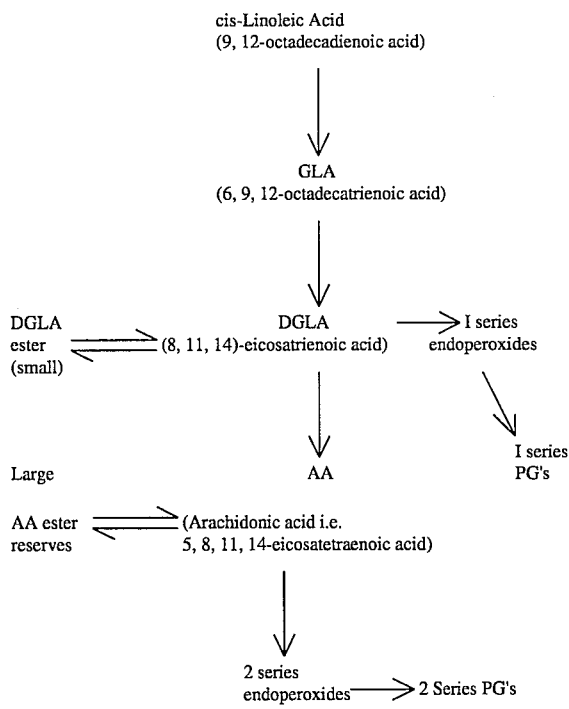

The broad outline of this pathway is well known, and it brings out clearly that a major function of essential fatty acids is to act as precursors for prostaglandins, 1-series PGs being formed from DGLA and 2-series PGs from arachidonic acid. Further, it has recently been found that the 22:4 n-6 acid produced from arachidonic acid gives rise to a series of homo-2-series PGs, though their importance is as yet unknown.

In addition to their role in PG synthesis, essential fatty acids are increasingly being seen as significant in themselves, primarily the acids of the n-6 series but also the acids of the n-3 series. The n-6 acids in particular are required in the body for the structure of membranes in and around cells, being believed to be necessary for maintaining normal flexibility, fluidity and permeability of such membranes.

The pathways of metabolism of the n-6 essential fatty acids and the related n-3 acids sharing, it is believed, common enzymes in the two pathways, are:

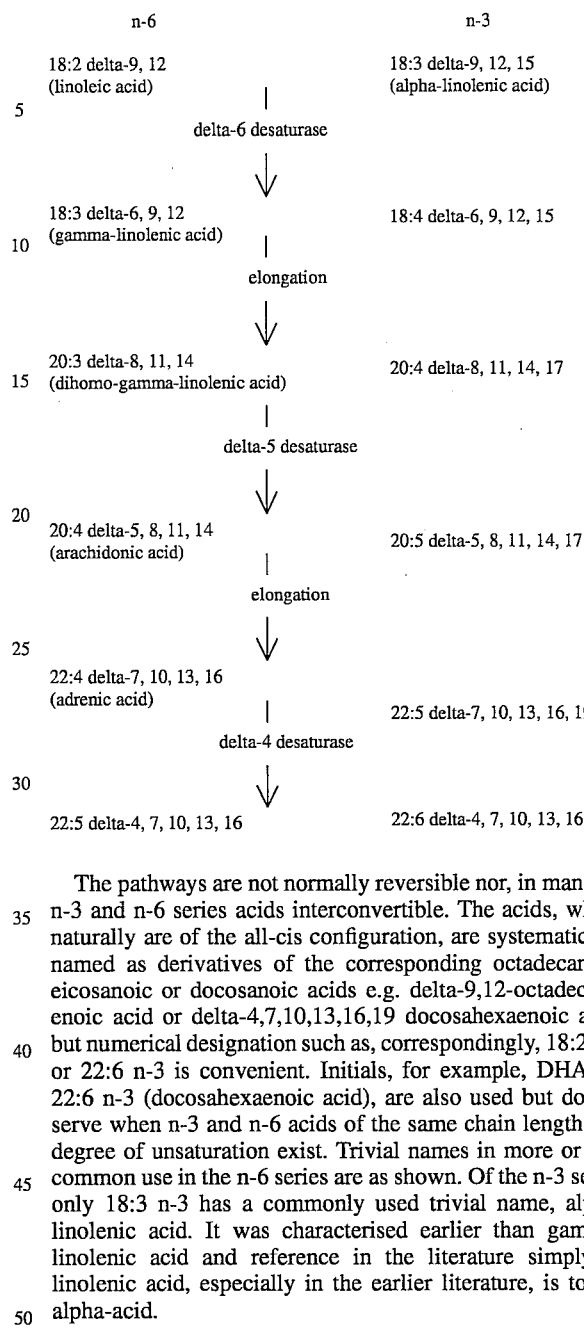

The pathways are not normally reversible nor, in man, are n-3 and n-6 series acids interconvertible. The acids, which naturally are of the all-cis configuration, are systematically named as derivatives of the corresponding octadecanoic, eicosanoic or docosanoic acids e.g. delta-9,12-octadecadienoic acid or delta-4,7,10,13,16,19 docosahexaenoic acid, but numerical designation such as, correspondingly, 18:2 n-6 or 22:6 n-3 is convenient. Initials, for example, DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature, is to the alpha-acid.

SPECIFIC BACKGROUND AND PROPOSAL

In addition to the general interst in EFAs referred to above there has been specific interest in their role in relation to interferons (alpha, beta and gamma), endogenous cytokines first discovered because of their anti-viral actions.

Interferons have been found not to exert such actions in cells in which the conversion of AA to prostaglandins is blocked by drugs or in which the cyclo-oxygenase enzyme is absent, see Pottathil et al Proc Natl Acad Sci USA 1980 77 (5437–5440) and Chandrabose et al, Science 1981 212 (329–331).

Further, there is increasing evidence that in many conditions there are low levels of AA in body tissues. One good example is atopic eczema, see Manku et al Br J Dermatol 1984 110 (643–8), a condition in which patients are known to be highly susceptible to viral infections. "It is likely that when AA levels are low, that the ability of the body to defend itself against viruses is reduced because the interferons cannot effectively exert their anti-viral actions."

We therefore propose that the anti-viral actions of interferons may be enhanced by administering AA itself, or a precursor of AA. The main dietary precursor of AA is linoleic acid, but in most of the situations in which AA levels have been found to be low, linoleic acid levels are normal or even elevated (e.g. Manku et al, above). The conversion of LA to its immediate metabolite GLA is slow at the best of times and can be further reduced by a whole variety of factors including atopic disorders, viral infections themselves, high alcohol intakes, and zinc deficiency. It is therefore appropriate to by-pass this step by administering either GLA, or its immediate metabolite DGLA, or AA itself. All will raise the body's concentration of AA and enable endogenous or exogenous interferons to work more effectively.

THE INVENTION

The invention therefore lies in:

1. A method of improving the therapeutic action of exogenous interferons by simultaneous or sequential co-administration of interferon in an appropriate dose with either GLA, or DGLA or AA or a combination of two or all of the fatty acids.

2. A method of improving the body's ability to eliminate viral infections by administering GLA or DGLA or AA to enable the body's endogenous interferons to function more effectively.

DOSE RANGES

Interferons alpha, beta or gamma, ranging from 500,000 to 500 million units/week preferably 2 million to 50 million units/week, very preferably 5 million to 25 million units/week in divided, daily or 2–5 times weekly doses.

A fatty acid chosen from GLA, DGLA or AA, in free acid, salt, ester, glyceride or equivalent form, each at a dose of 1 mg to 100 g/day, preferably 10 mg to 10 g and very preferably 100 mg to 3 g.

The interferons may be administered intramuscularly or intravenously or by any other appropriate route. They may also be applied topically in concentrations ranging from 100,000 to 10 million units per ml. The EFAs may be administered orally or parenterally or by a convenient route, or applied topically in concentrations ranging from 1 mg to 300 mg/ml.

FORMS OF EFAs

Convenient derivatives of gamma-linolenic acid and dihomo-gamma-linolenic acid and arachidonic acid in the invention include salts, amides, esters including glyceride esters and alkyl (e.g. C1 to C4) esters, and phospholipids. Such pharmaceutically acceptable and physiologically equivalent derivatives are to be taken as included when reference to any of the acids is made herein, including in the claims. Equivalence is demonstrated by entry into the pathway quoted in the general discussion earlier, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat or other tissue by standard techniques, for example those of Pelick et al p. 23, Analysis of Lipids and Lipoproteins' Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography on silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° to 190° at 2° C./min. Detector temperature is 220° and injector temperature 200° C. Retention times and peak areas are automatically computed by Hewlett-Packard Level 4 integrator. Peaks are identified by comparison with standard fatty acid methyl esters.

The invention is chiefly described in terms of use of pharmaceutical compositions, but it will be understood that the gamma-linolenic and other acids, being in the nature of dietary supplements, could be incorporated in a dietary margarine or other foodstuff for use by those requiring enhancement of the effects of interferons.

FORMS AND SOURCES OF GAMMA-LINOLENIC AND OTHER ACIDS

Ordinary pharmaceutical compositions may be produced for use in the invention by associating the natural or synthetic acids, as such or as derivatives, with an acceptable pharmaceutical vehicle. It is, however, at present convenient to incorporate at least the gamma-linolenic acid into compositions in the form of an available oil having a high gamma-linolenic acid content, hence reference to 'oil' herein.

SOURCES OF EFAa

At the present time known natural sources of oils having a high gamma-linolenic acid content are few. One source of oils currently available is the seed of Evening Primrose species such as *Oenothera biennis L* and *Oenothera lamarckiana*, the oil extract therefrom containing gamma-linolenic acid (about 8%) and linoleic acid (about 72%) in the form of their glycerides together with other glycerides (percentages based on total fatty acids). Other sources of gamma-linolenic acids are Borage species such as *Borage officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

As preservative, alpha-tocopherol is added to the oil in a concentration 0.1%.

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

A source of DGLA is a Mortierella (fungus) species *Mortierella alpina* (Shimizu et al, JAOCS 66 No 2 pp 237–241 February 1989) though it is not on the market and in practice one will use GLA, readily converted in the body to DGLA in any event. If AA is required it is available, derived for example from slaughter houses as the considerable ester reserves present in animal tissues.

The acids as such can be isolated from the natural, usually glyceride, sources by, for example, saponification under mild non-oxidising conditions followed by preparative gas liquid chromatography. Synthesis of the acids is difficult but not impossible and provides another source.

PHARMACEUTICAL PRESENTATION

Essential fatty acids for use in the invention, as discussed earlier, are conveniently in a form suitable for oral, rectal or parenteral administration in a suitable pharmaceutical vehicle, as discussed in detail for example in Williams British Patent Specification No. 1,082,624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparations. Alpha-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

Among virus infections treated by the method of the present invention are those caused by rhinoviruses, herpes viruses, cytomegaloviruses and papillomaviruses including herpes and other infections treatable by topical preparations. Examples of administration against these conditions are, also effective in anti-cancer use and anti-inflammatory use against rheumatoid arthritis or other inflammatory diseases, as follows:

1. Administration of 3 million units of alpha-interferon per day as a parenteral preparation together with oral administration of hard gel capsules containing 280 mg GLA and 100 mg EPA at the rate of 6/day.

2. Administration intravenously of a solution containing 3 million units of interferon per 500 ml, together with oral administration of 2 g of lithium-GLA and 1 g of sodium-EPA, in the form of hard gelatin capsules.

3. Topical or intra-lesional administration of 1 million units of interferon/day combined with oral administration of hard gel capsules containing 300 mg of DGLA and 200 mg of EPA and 100 mg of DHA, 6 capsules/day.

4. Topical administration of a solution containing 1 million units interferon/2 ml and 50 mg of lithium- DGLA and 50 mg of sodium-EPA/2 ml, to appropriate lesions twice per day.

I claim:

1. A method of enhancing the anti-viral effect of interferons comprising administering to a person suffering from a viral infection a medicament containing a fatty acid selected from the group consisting of gamma-linolenic acid, dihomo-gamma-linolenic acid, arachidonic acid and mixtures thereof, in association with a medicament containing one or more interferons.

2. The method of claim 1 wherein said fatty acid is administered topically in amounts from 1 mg to 300 mg/ml and said interferon is administered in amounts from 100,000 to 10 million units/ml.

3. The method of claim 1 wherein the said fatty acid and said interferon are formulated in the same medicament.

4. The method of claim 1, wherein amounts of interferons alpha, beta or gamma, range from 500,000 to 500 million units/week in divided, daily or 2 to 5 times weekly doses, and said fatty acid is each administered at a dose rate of 1 mg to 100 g/day.

5. The method of claim 4 wherein the amount of said interferon is administered in a range from 2 million to 50 million units/week.

6. The method of claim 4 wherein the amount of said interferon is administered in a range from 5 million to 25 million units/week.

7. A method of enhancing the anti-viral effect of endogenous interferons comprising administering to a person suffering from a viral infection a medicament containing a fatty acid selected from the group consisting of gamma-linolenic acid, dihomo-gamma-linolenic acid, arachidonic acid and or mixtures thereof.

8. The method of claim 7, wherein said fatty acid is each administered at a dose rate of 1 mg to 100 g/day.

9. The method of claim 4 or 8 wherein the amount of said fatty acid is administered in a range from 10 mg to 10 g/day.

10. The method of claim 4 or 8 wherein the amount of said fatty acid is administered in a range from 100 mg to 3 g/day.

11. The method of claim 7 wherein said fatty acid is administered topically in amounts from 1 mg to 300 mg/ml.

* * * * *